United States Patent [19]

Rakhit

[11] 4,316,885
[45] Feb. 23, 1982

[54] ACYL DERIVATIVES OF RAPAMYCIN

[75] Inventor: Sumanas Rakhit, Dollard des Ormeaux, Canada

[73] Assignee: Ayerst, McKenna and Harrison, Inc., Montreal, Canada

[21] Appl. No.: 181,252

[22] Filed: Aug. 25, 1980

[51] Int. Cl.$^3$ ..................... A61K 35/74; C07D 491/14
[52] U.S. Cl. ........................................ 424/122; 546/90
[58] Field of Search ........................... 424/122; 546/90

[56] References Cited

U.S. PATENT DOCUMENTS

| 3,929,992 | 12/1975 | Sehgal et al. | 424/122 |
| 3,993,992 | 12/1975 | Sehgal et al. | 424/122 |

FOREIGN PATENT DOCUMENTS

| 877700 | 1/1980 | Belgium | 424/122 |

OTHER PUBLICATIONS

Vezina et al., Journal of Antibiot., vol. 28, pp. 721–726 (1975).
Sehgal et al., Journal of Antibiot., vol. 28, pp. 727–732 (1975).
Neil et al., Canadian Journal of Chem., vol. 56, pp. 2491–2492 (1978).
Baker et al., Journal of Antibiot., vol. 31, pp. 539–545 (1978).
Martel et al., Canadian Journal of Physiol., vol. 55, pp. 48–51 (1977).

Primary Examiner—Alan L. Rotman
Attorney, Agent, or Firm—Arthur E. Wilfond

[57] ABSTRACT

Disclosed are monoacyl and diacyl derivatives of rapamycin, processes for their preparation, methods of using the derivatives and pharmaceutical compositions of the derivatives. The derivatives are useful, inter alia, as antifungal antibiotics.

5 Claims, No Drawings

ACYL DERIVATIVES OF RAPAMYCIN

BACKGROUND OF THE INVENTION

This invention relates to novel monacyl and diacyl derivatives of rapamycin, to processes for their preparation, to methods of using the derivatives and to pharmaceutical compositions of the derivatives. The derivatives are useful as antifungal antibiotics.

Rapamycin is an antifungal antibiotic described by C. Vezina et al., J. Antibiot., 28, 721 (1975), S. N. Sehgal et al., J. Antibiot., 28, 727 (1975), S. N. Sehgal et al., U.S. Pat. No. 3,929,992, issued Dec. 30, 1975 and S. N. Sehgal et al., U.S. Pat No. 3,993,749, issued Nov. 23, 1976. The latter two patents are herein incorporated by reference. The structure of rapamycin is described by D. C. Neil Swindells, et al., Can. J. Chem., 56, 2491 (1978). Rapamycin is extracted from a streptomycete (Streptomyces hygroscopicus) isolated from an Easter Island soil sample and is particularly effective against *Candida albicans* both in vitro and in vivo, H. A. Baker et al., J. Antibiot., 31, 539 (1978). A report by R. R. Martel et al., Can. J. Physiol., 55, 48 (1977) describes the use of rapamycin for the prevention of the development of experimental immunopathies. Recently, rapamycin was shown to be an effective agent for treating carcinogenic tumors in a mammal by S. N. Sehgal and C. Vezina, U.S. patent application Ser. No. 957,626, filed Nov. 3, 1978. In Belgium, a corresponding application of the latter application issued as Belgium Pat. No. 877,700 on Jan. 14, 1980.

SUMMARY OF THE INVENTION

The compounds of this invention are monoacyl or diacyl derivatives of rapamycin wherein the acyl is selected from the group of aliphatic acyl having 1 to 10 carbon atoms; benzoyl; benzoyl mono- or disubstituted with lower alkyl, halo, lower alkoxy, hydroxy or trifluoromethyl, and phenyl substituted aliphatic acyl wherein the aliphatic acyl portion has 2 to 10 carbon atoms and the phenyl is unsubstituted or mono- or disubstituted with lower alkyl, halo, lower alkoxy, hydroxy or trifluoromethyl.

Preferred compounds of this invention are monoacyl or diacyl derivatives of rapamycin wherein the acyl is selected from an aliphatic acyl having 2 to 6 carbon atoms.

An antifungal composition is provided by combining an antifungally effective amount of the monoacyl or diacyl derivative of rapamycin with a pharmaceutically acceptable carrier.

The monoacyl and diacyl derivatives of rapamycin inhibit the growth of pathogenic fungi in a mammal by administering to the mammal an effective antifungal amount of the monoacyl or diacyl derivative of rapamycin.

DETAILED DESCRIPTION OF THE INVENTION

The term "lower alkyl" as used herein means straight chain alkyl radicals containing from one to six carbon atoms and branched chain alkyl radicals containing from three to four carbon atoms and includes methyl, ethyl, propyl, 1-methylethyl, butyl, 1,1-dimethylethyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexanoxy and the like.

The term "halo" as used herein means halogens and includes fluorine, chlorine, bromine and iodine, unless stated otherwise.

The term "aliphatic acyl" as used herein means straight chain 1-oxoalkyl radicals containing from one to ten carbon atoms and branched chain 1-oxoalkyl radicals containing four to ten carbon atoms and includes formyl, acetyl, 1-oxopropyl, 1-oxobutyl, 2,2-dimethyl-1-oxopropyl, 1-oxohexyl, 1-oxo-3-ethylpentyl and the like.

The term "organic proton acceptor" as used herein means the organic bases or amines, for instance, triethylamine, pyridine, N-ethylmorpholine, 1,5-diazabicyclo[4.3.0]non-5-ene and the like.

The monoacyl and diacyl derivatives of rapamycin are useful as antifungal agents against pathogenic fungi; for example *Candida albicans*. The inhibitor activity of the derivatives are especially pronounced against *Candida albicans*. Against this fungi, the monoacetyl derivative exhibits a MIC of 0.04 mcg/ml and the diacetyl derivative exhibits a MIC of 2.5 mcg/ml.

The antifungal activity of the derivatives are demonstrated in standard tests used for this purpose, for example, in the tests described in "Antiseptics, Disinfectants, Fungicides and Sterilization", G. F. Reddish, Ed., 2nd ed., Lea and Febiger, Philadelphia, 1957 or by D. C. Grove and W. A. Randall in "Assay Methods of Antibiotics", Med. Encycl. Inc., New York 1955.

When the rapamycin derivative of this invention is employed as an antifungal agent in a mammal, it can be used alone or in combination with pharmaceutically acceptable carriers, the proportion of which is determined by the solubility and chemical nature of the compound, chosen route of administration and standard biological practice. For example, an antifungally effective amount of the derivatives can be administered orally in solid form containing such excipients as starch, sugar, certain types of clay and so forth. Similarly, such an amount can be administered orally in the form of solutions or suspensions, or the derivative can be injected parenterally. For parenteral administration the derivative can be used in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The dosage of the present derivative will vary with the form of administration and the particular derivative chosen. Furthermore, it will vary with the particular host under treatment. Generally, treatment is initiated with small dosages substantially less than the optimum dose of the derivative. Thereafter, the dosage is increased by small increments until the optimum effect under the circumstances is reached. In general, the derivative of this invention is most desirably administered at a concentration level that will generally afford antifungally effective results without causing any harmful or deleterious side effects and preferably at a level that is in a range of from about 1.0 mg to about 250 mg per kilo per day, although as aforementioned variations will occur. However, a dosage level that is in the range of from about 10 mg to about 100 mg per kilo per day is most desirably employed in order to achieve effective results.

In addition, the derivative can be employed topically. For topical application it may be formulated in the form of solutions, creams or lotions in pharmaceutically acceptable vehicles containing 0.1–5 percent, preferably 2 pecent of the agent, and may be administered topically to the infected area of the skin.

The derivative also can be used for cleaning and disinfecting laboratory equipment, surgical instruments, locker rooms, or shower rooms of sensitive fungus organisms. For such purposes it is preferred to use 0.1–10% solutions of the derivative in a lower alkanol, preferably methanol, diluted with 10–100 volumes of water containing 0.001–0.1% of a non-ionic surface-active agent, for example, polysorbate 80 U.S.P., immediately before applying it to the objects to be cleaned and disinfected.

The acyl derivatives of rapamycin are prepared by the acylation of rapamycin. Acylation of rapamycin with an acylating agent selected from an alkanoyl iodide, bromide or chloride having two to ten carbon atoms, benzoyl bromide or chloride, benzoyl bromide or chloride mono- or disubstituted with lower alkyl, halo, lower alkoxy, hydroxy or trifluoromethyl, or phenyl substituted alkanoyl bromide or chloride wherein the alkanoyl portion has two to ten carbon atoms and the phenyl is unsubstituted or mono- or disubstituted with lower alkyl, halo, lower alkoxy, hydroxy or trifluoromethyl in the presence of an organic proton acceptor, preferably triethylamine or pyridine, at 0° to 50° C. for 0.5 to 10 hours gives the corresponding monoacyl or diacyl derivative of rapamycin wherein the acyl portion contains two to ten carbon atoms. Replacement of the above described acylating agent with the corresponding anhydride also gives the corresponding monoacyl or diacyl derivative of rapamycin. The above acylations can be conducted in an inert organic solvent such as benzene, chloroform or dichloromethane or an excess of the organic proton acceptor can serve as the solvent. In the case of preparing the mono- and diformyl derivative, a preferred reagent is formic acetic anhydride (prepared from acetic anhydride and formic acid). The formyl derivatives can also be obtained by the use of formic acid in the presence of an acid catalyst, for instance, p-toluenesulfonic acid, sulfuric acid or perchloric acid. Use of about 0.7 to 1.5 molar equivalents of the acylating agent gives a separable mixture of the monoacyl and diacyl derivatives wherein the monoacyl derivative predominates whereas use of about 1.5 to 5 molar equivalents of the acylating agent gives a separable mixture of the monoacyl and diacyl derivatives wherein the diacyl derivative predominates. When the acylation involves acetylation, a preferred method of acetylation is the reaction of rapamycin with acetic anhydride in an excess of the organic proton acceptor at 0° to 10° C. for about one to three hours to obtain a separable mixture of the monoacetyl and diacetyl derivatives of rapamycin.

The following example illustrates further this invention.

EXAMPLE 1

Monoacetyl and Diacetyl Derivatives of Rapamycin

A solution of 300 mg of rapamycin in 5 ml of dry pyridine was cooled in an ice bath. To this solution, 2.5 ml of acetic anhydride was added and the mixture was stirred at 0° to 5° C. for 2hr. The excess of anhydride was decomposed by careful addition of methanol and the mixture was poured into ice containing 2N hydrochloric acid. The precipitated solids were extracted with ethyl acetate. The ethyl acetate extract was washed with water, dried over sodium sulfate and evaporated. The oily residue was chromatographed over silica gel using 20% ethyl acetate in benzene. The appropriate initial fractions were collected, evaporated and crystallized from chloroform-hexane to give rapamycin diacetate (0.165 g): mp 92°–93° C.; ir (CHCl$_3$) 3400, 1730, 1640 and 1620 cm$^{-1}$; uv max (MeOH) 288 ($\epsilon$=366), 227 ($\epsilon$=484) and 267 nm ($\epsilon$=363); and nmr (CDCl$_3$) $\delta$2.05 (s, 3H). The appropriate later fractions were collected, evaporated and crystallized from benzene-hexane to give rapamycin monoacetate (0.058 g): mp 101°–120° C.; ir (CHCl$_3$) 3400, 1730, 1640 and 1620 cm$^{-1}$; uv max (MeOH) 288 ($\epsilon$=374), 277 ($\epsilon$=494) and 267 nm ($\epsilon$=372); and nmr (CDCl$_3$) $\delta$2.05 (s, 3H) and 2.1 (s, 3H).

I claim:

1. A monacetyl or diacetyl derivative of rapamycin wherein the monoacetyl derivative has mp 101°–102° C.; ir (CHCl$_3$) 3400, 1730, 1640 and 1620 cm$^{-1}$; uv max (MeOH) 288 ($\epsilon$=374), 277 ($\epsilon$=494) and 267 nm ($\epsilon$=372); and nmr (CDCl$_3$) $\delta$2.05 (s, 3H) and 2.1 (s, 3H) and the diacetyl derivative has mp 92°–93° C.; ir (CHCl$_3$)3400, 1730, 1640 and 1620 cm$^{-1}$; uv max (MeOH) 288 ($\epsilon$=366), 227 ($\epsilon$=484) and 267 nm ($\epsilon$=363); and nmr (CDCl$_3$) $\epsilon$2.05 (s, 3H).

2. Rapamycin monoacetate, as claimed in claim 1.

3. Rapamycin diacetate, as claimed in claim 1.

4. An antifungal composition, which comprises an antifungal effective amount of a monoacyl or diacetyl derivative of rapamycin, as claimed in claim 1, and a pharmaceutically acceptable carrier.

5. A method of inhibiting the growth of pathogenic fungi in a mammal, which comprises administering to said mammal an antifungally effective amount of a monoacetyl or diacetyl derivative of rapamycin, as claimed in claim 1.

* * * * *